United States Patent [19]

Carmosin et al.

[11] Patent Number: 4,689,329
[45] Date of Patent: Aug. 25, 1987

[54] 5-SUBSTITUTED OCTAHYDROINDOLIZINE ANALGESICS COMPOUNDS AND 7-KETO INTERMEDIATES

[75] Inventors: Richard J. Carmosin, Red Hill; John R. Carson, Norristown, both of Pa.

[73] Assignee: McNeilab, Inc., Fort Washington, Pa.

[21] Appl. No.: 826,167

[22] Filed: Feb. 4, 1986

[51] Int. Cl.⁴ .................... A61K 31/40; C07D 471/04
[52] U.S. Cl. .................................. 514/299; 544/180; 544/216; 544/238; 544/242; 544/335; 544/336
[58] Field of Search ................. 546/112, 183; 514/299

[56] References Cited

U.S. PATENT DOCUMENTS 4,205,074   5/1980   Kato et al. ................. 546/112 X
4,559,346  12/1985   King ............................... 514/299
4,582,836   4/1986   Carmosin et al. ........ 546/112 X

FOREIGN PATENT DOCUMENTS 0139378  10/1980   Japan ............................... 514/299

OTHER PUBLICATIONS

Chem. Abstracts, vol. 52, pp. 18409b to 18410e (1958).
Y. Nagai et al.; Chem. Pharm. Bull., 27 (5), pp. 1159–1168 (1979).
H. Stetter et al.; the Journal of Heterocyclic Chemistry, 14, pp. 573–581 (1977).
M. G. Reinecke et al.; the Journal of Organic Chemistry, 31, pp. 4215–4220 (1966).
M. E. Rogers et al.; the Journal of Medicinal Chem., vol. 18, No. 11, pp. 1126–1130 (1975).
F. Lions et al.; Proc. Royal Soc., N. S. Wales 73, pp. 240–252 (1940).

Primary Examiner—Joseph Paul Brust
Attorney, Agent, or Firm—David J. Levy

[57] ABSTRACT

Octahydroindolizidines and corresponding ketones of the formulae (I) and (II):

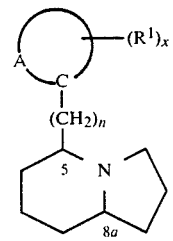

(I)

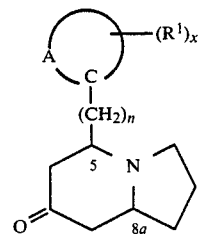

(II)

where A is a 3–7 carbon or hetero-containing ring, $R^1$ is a substituent, n is 0–6 and x is 0–3. Also, pharmaceutical compositions for treating pain containing (I) or (II) and methods for synthesis and use as well as novel intermediates in the synthesis.

27 Claims, No Drawings

5-SUBSTITUTED OCTAHYDROINDOLIZINE ANALGESICS COMPOUNDS AND 7-KETO INTERMEDIATESA

The present invention comprises certain octahydroindolizine compounds including acid addition salts thereof, methods for their preparation and use, pharmaceutical compositions and intermediates used in their synthesis. 3-Aryloctahydroindolizines are disclosed by I. Murakoshi in Yakugaku Zasshi, 78, pages 594–7 (1958) which appears in Chemical Abstracts at Volume 52, pages 18409b to 18410e (1958); by Y. Nagai et al in Chem. Pharm. Bull., 27 (5), pages 1159–1168 (1979); and H. Stetter et al in the Journal of Heterocyclic Chemistry, 14, pages 573–581 (1977). 1-Phenylindolizine is disclosed by M. G. Reinecke et al in the Journal of Organic Chemistry, 31, pages 4215–4220 (1966). Quinolizidines are shown by M. E. Rogers in the J. of Medicinal Chem., Vol. 18, No. 11, pages 1126–1130 (1975) while substituted octahydroindolizines are disclosed by F. Lions in Proc. Royal Soc., N. S. Wales 73, pages 240–252 (1940).

SUMMARY OF THE INVENTION

Compounds of the present invention are of the following formula (I):

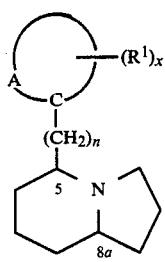

(I)

and acid addition salts wherein A represents the atoms necessary to form a 3 to 7 membered carbocyclic or nitrogen-containing heterocyclic aromatic or saturated ring, n is 0–6, $R^1$ is a substituent and x is 0–3. Also included within the invention are pharmaceutical compositions, methods for the synthesis of formula (I) compounds and intermediates used in such syntheses, in particular those of the formula (II) which are also active as analgesics.

DETAILED DESCRIPTION OF THE INVENTION

Compounds of the present invention are octahydroindolizines of the following formula (I):

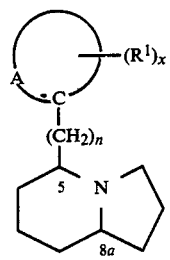

(I)

wherein
A represents the atoms necessary to form a ring system selected from the group consisting of phenyl, naphthyl, cycloalkyl, cycloalkenyl, thienyl, furanyl, pyrrolyl, pyridinyl, pyridazinyl, pyrimidinyl, pyrazinyl or triazinyl;

$R^1$ is independently cyano; halogen; alkyl; alkyloxy; alkylthio; phenylthio; phenylthio substituted by acetamido, halo or alkyl; haloalkyl; alkenyl; alkynyl; or cycloalkenyl; or $R^1$ is alkyl, alkenyl or alkynyl substituted by hydroxy;

n is the integer 0, 1, 2, 3, 4, 5 or 6; and x is the integer 0, 1, 2 or 3, provided that when A is phenyl and n is 0, x is 1, 2 or 3, and the pharmaceutically-acceptable acid-addition salts thereof.

Pharmaceutical compositions of the invention comprise the formula (I) compounds as defined above also including those wherein when A is phenyl n is 0 and x is 0, and methods for the use of such pharmaceutical compositions. In more detail, A is phenyl; naphthyl; cycloalkyl of about 3 to 7 carbons such as cyclopentyl and cyclohexyl; cycloalkenyl of about 3 to 7 carbons such as cyclopentenyl and cyclohexenyl, e.g. 1-cyclohexen-1-yl; thienyl such as 2- or 3-thienyl; furanyl such as 2- or 3-furanyl; pyrrolyl such as 2- or 3-pyrrolyl; pyridinyl such as 2-, 3- or 4-pyridinyl; pyridazinyl such as 3- or 4-pyridazinyl; pyrimidinyl such as 2- 4- or 5-pyrimidinyl; pyrazinyl such as 2-pyrazinyl; or triazinyl such as 1,2,3-triazinyl attached at the 4 or 5 position thereof, 1,2,4-triazinyl attached at the 3, 5 or 6 position or 1,3,5-triazinyl attached at the 2 position.

$R^1$, in more detail, is independently, e.g., two different $R^1$ moieties may be attached to the A ring when x is 2, cyano; halogen such as fluoro, chloro, bromo and iodo; alkyl of about 1 to 8 carbons such as methyl, ethyl, n-propyl and sec-butyl; alkoxy of about 1 to 8 carbons such as methoxy, ethoxy and iso-propoxy; alkylthio of about 1 to 8 carbons such as methylthio and ethylthio; phenylthio; phenylthio substituted by particularly a single moiety of acetamido, fluoro, chloro, bromo, iodo or alkyl of about 1 to 6 carbons such as methyl and ethyl, such substitution being at the o-, m- or p-position, most particularly at the p-position; haloalkyl of about 1 to 8 carbons independently substituted by one or more of fluoro, chloro, bromo or iodo such as trifluoromethyl and 2,2,2-trifluoroethyl; alkenyl of about 2 to 8 carbons such as ethenyl, 1-propenyl and 2-propenyl; alkynyl of about 2 to 8 carbons such as ethynyl, 1-propargyl and 2-propargyl; cycloalkenyl of about 3 to 7 carbons such as cyclopropenyl and 1-cyclohexenyl; or such alkyl, alkenyl or alkynyl substituted by hydroxy such as 3-hydroxy-n-butyl, 3-hydroxy-1-n-butenyl and 6-hydroxy-1-n-hexynyl.

n is an integer from 0–6, particularly 0–2. When A is other than a phenyl ring, n is particularly 0.

x is 0–3 and is particularly 1 when $R^1$ is other than halo, alkoxy or alkyl.

Particular A-$R^1$ ring systems for formula (I) include phenyl rings where x is 1, 2 or 3 and $R^1$ is halogen such as ortho-halophenyl, e.g., para-bromophenyl, ortho-bromophenyl, 2,4-dibromophenyl, 2,4-dimethylphenyl, meta-fluorophenyl, para-acetamidophenylthio, ortho-bromophenyl, 2-chloro-6-fluorophenyl, and 2,6-difluorophenyl and particularly where x is 1, 2 or 3, e.g. 1, and at least one $R^1$ substituent is at the ortho position of the phenyl ring relative to the point of attachment of the phenyl ring to the —$(CH_2)_n$— moiety.

Particular invention compounds of formula (I) shown in the Examples include the following:

5-cyclohexyloctahydroindolizine,
octahydro-5-(2-phenylethyl)indolizine,
5-(4-bromophenyl)octahydroindolizine,
5-(2,4-dichlorophenyl)octahydroindolizine,
5-(2-bromophenyl)octahydroindolizine,
5-(2,4-dimethylphenyl)octahydroindolizine,
octohydro-5-[(3-trifluoromethyl)phenyl)]indolizine, and
N-[[[4-(trans-octahydro-5-indolizinyl)phenyl]thio]phenyl] acetamide.

Also within the scope of the invention are 7-keto intermediates of the following formula (II):

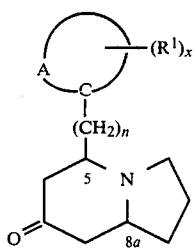
(II)

wherein A, $R^1$, n and x are as described for formula (I) and the isomeric considerations described herein.

Particular invention compounds of formula (II) shown in the Examples are the following:
5-cyclohexylhexahydro-7(8H)-indolizinone,
hexahydro-5-(2-phenylethyl)-7(8H)-indolizinone,
5-(4-bromophenyl)hexahydro-7(8H)-indolizinone,
5-(2,4-dichlorophenyl)hexahydro-7(8H)-indolizinone,
5-(2-bromophenyl)hexahydro-7(8H)-indolizinone,
5-(2,4-dimethylphenyl)hexahydro-7(8H)-indolizinone, and
hexahydro-5-[(3-trifluoromethyl)phenyl)]-7(8H)-indolizinone.

Various isomers are possible in formulae (I) and (II) compounds and the present invention includes all such individual enantiomers, diastereomers, racemates and other isomer ratios. Specifically, such compounds have 5-substitution and, may exist in the following 4 forms: α-5-R-α-8a-H; α-5-R-β-8a-H; β-5-R-α-8aH; and β-5-R-β-8a-H.

Resolution of enantiomers, of course, results in a single enantiomer without its enantiomeric mirror image and these individual enantiomers are designated by (−) or (+) according to the direction in which they rotate polarized light. When used in the present application, a "trans" compound is one wherein the 5-position —$(CH_2)_n$— substituent and the 8a hydrogen are trans to each other, e.g. the racemate or either enantiomer. Thus, in the trans molecule, the hydrogens at the 5 and 8a position are cis to each other. In the reaction sequences described in the examples, the trans compound is somewhat easier to isolate and usually is recovered first on silica flash chromatography. However, the cis compound is produced and can be isolated by standard recovery techniques.

Representative salts of the compounds of formulae (I) and (II) which may be used include those made with acids such as hydrochloric, hydrobromic, hydroiodic, perchloric, sulfuric, nitric, a phosphoric, acetic, propionic, glycolic, lactic pyruvic, malonic, succinic, maleic, fumaric, malic, tartaric, citric, benzoic, cinnamic, mandelic, methanesulfonic, ethanesulfonic, hydroxyethanesulfonic, benezenesulfonic, p-toluene sulfonic, cyclohexanesulfamic, salicyclic, p-aminosalicylic, 2-phenoxybenzoic, 2-acetoxybenzoic or a salt made with saccharin. Such salts can be made by reacting the free base of (I) with the acid and recovering the salt. Also within the scope of the invention are the various hydrate and solvate forms and the crystal polymorphs of the compounds of formulae (I) and (II).

Compounds of this invention may be prepared via the route shown in the F. Lions publication (1940) mentioned above or by reference to the following Reaction Scheme:

Reaction Scheme

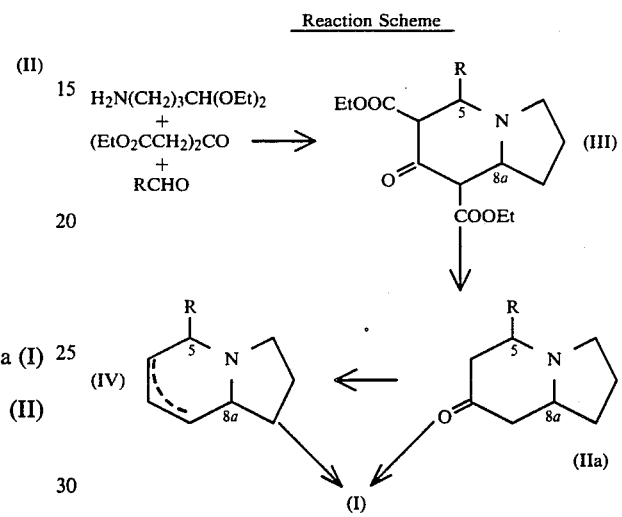

An aldehyde RCHO wherein R is —$(CH_2)_n$—C—A—$(R^1)_x$, is condensed with aminobutyraldehyde diethyl acetal and diethyl acetone dicarboxylate in aqueous mineral acid at room temperature for several days to give a crude keto-diester of formula (III) which is not isolated. Heating (III) with aqueous mineral acid affords the ketone (IIa). Wolff-Kischner reduction of (II) with hydrazine (or semicarbazide) and an alkali metal hydroxide gives the invention product of formula (I). Alternatively, Clemmenson reduction with zinc amalgam and HCl can give an olefin or a mixture of olefins (IV) which are reduced catalytically to (I). In (IV), the dashed line indicates a single double bond between the 6 and 7 positions or the 7 and 8 positions.

A compound of type (I) where the A-ring is phenyl and $R^1$ is halo may be transformed to other derivatives, for instance to a substituted phenylthio derivative by treatment with an arylthiol in the presence of base and a palladium (O) catalyst.

The groups $R^1$ may be attached directly to the —C—A function during the synthesis of the octahydroindolizine ring. Alternatively they may be attached following the synthesis of the 5-substituted octahydroindolizine. For instance a 5-(halophenyl)octahydroindolizine may be converted to the corresponding lithium derivative by reaction with an alkyllithium. 5-(2-Lithiophenyl)octahydroindolizine on reaction with dimethyldisulfide affords 3-(2-methylthiophenyl) octahydroindolizine. Reaction of the lithio derivative with cyclohexanone affords the derivative with a 1-cyclohexanol attached. A 5-(2-halophenyl)octahydroindolizine, when subjected to palladium catalyzed coupling with cuprous cyanide or a 1-alkyne gives the corresponding cyano or alkynyl derivative. Compounds of formula (I) wherein the A-ring is cyclohexyl or substituted cyclohexyl may be prepared by catalytic hydrogenation of the appropriate phenyl compound over a noble metal catalyst, for example rhodium, ruthenium or platinum, provided, however, that such hydrogenation cannot be carried out when a sulphur atom is present in the molecule.

In the Reaction Scheme, a mixture of diastereoisomers is produced in which the biologically more active $5\alpha, 8a\beta$ diastereomers, the diastereomeric pair of enantiomers bearing the hydrogens at 5 and 8a are on the same face, is predominant. The diastereomers may be separated by chromatography on silica or by fractional crystallization.

If desired, the compounds of formula (I) may be resolved into optical isomers, i.e. enantiomers, by fractional crystallization of a salt with an optically active acid such as, for instance, di-$p$-toluoyl tartaric acid.

The activity of compounds (I) of the invention and intermediates (II) as analgesics may be demonstrated by an abdominal constriction assay, a tail flick assay or a hot plate assay as described below:

Mouse Acetylcholine-Bromide-Induced Abdominal Construction Assay:

The mouse acetylcholine-induced abdominal constriction assay, as described by Collier et al. in Brit. J. Pharmacol. Chem. Ther., 32:295-310, 1968, with minor modifications was one test used to assess analgesic potency. The test drugs or appropriate vehicle were administered orally (p.o.) and 30 minutes later the animals received an intraperitoneal (i.p.) injection of 5.5 mg/kg acetylcholine bromide (Matheson, Coleman and Bell, East Rutherford, NJ). The mice were then placed in groups of four into glass bell jars and observed for a ten minute observation period for the occurrence of a writhe (defined as a wave of constriction and elongation passing caudally along the abdominal wall, accompanied by a twisting of the trunk and followed by extension of the hind limbs). The percent inhibition of writhing (equated to % analgesia) was calculated as follows: The % inhibition of writhing, i.e., % analgesia, is equal to the difference between the No. of control animals writhing and the No. of drug-treated animals writhing times 100 divided by the No. of control animals writhing.

At least 20 animals were used for control and in each of the drug treated groups. Four doses were used to determine each dose response curve and $ED_{50}$ (that dose which inhibits writhing by 50%). The $ED_{50}$ values and their 95% fiducial limits were determined by a computer assisted probit analysis.

Mouse Tail Flick Assay:

The tail flick assay, originally described by D'Amour and Smith in J. Pharmacol. Exp. Ther. 72:74-79, 1941 with modifications, see Vaught and Takemori, J. Pharmacol. Exp. Ther. 208:86-90, 1979 was used to assess analgesic potency. A mouse tail is placed in the path of a focused beam of light produced by an ITTC, Inc. Mod-33 Analgesia Meter. The animal responds to this noxious stimulus produced by the beam of light by "flicking" or removing its tail from the path of the stimulus. The timer and light is manually shut off when the animal responds in such a manner. The reaction time is recorded. At appropriate times following drug administration (by the desired route) the above procedure is repeated and these reaction times compared to pre-drug reaction times. A reaction time for drug-treated animals greater than three standard deviations from the mean of the control reaction times for all the animals in the group was the criterion for an analgesic response.

At least three doses with 10 animals per dose were used to construct dose response curves. A SAS Probit Analysis was used to generate $ED_{50}$ (that dose which produces analgesia in 50% of the animals) values and 95% fiducial limits (as described previously).

Mouse Hot Plate Assay:

The hot plate assay was one test used to assess analgesic potency, see Vaught and Chipkin, Eur. J. Pharmacol. 79, 167-173, 1982 and references therein. In these experiments the hot plate apparatus (Technilab Instruments, Inc.) was maintained at $48 \pm 0.05°$ C. The response measure was the time interval between the animal being placed on the heated surface and licking or shaking its hind paw. Test drug was administered by the desired route, and at appropriate times following drug administration, reaction times redetermined. The criterion for an analgesic response and the method for calculation of $ED_{50}$ and 95% fiducial limits is as that described for the tail flick assay. Animals: In all experiments male, virus-free, Swiss CD-1 mice (18-24 g) purchased from Charles River Breeders were used. They were allowed food and water ad libitum and were used only once.

In the Mouse Acetylcholine Assay described above, the $ED_{50}$ values for the compounds produced in the Examples were as follows: about 2.5 mg/kg of body weight, p.o. for Example 8; about 6.0 mg/kg p.o. for Example 4b; and about 9.7 mg/kg p.o. for Example 1b. All products of Formula (I) had a duration of activity of at least 2 hours.

In the Mouse Tail Flick Assay, the compound produced in Example 8 had an $ED_{50}$ value of about 45.1 mg/kg of body weight, i.p.

In the Mouse Hot Plate Assay, the compound produced in Example 8 had an $ED_{50}$ value of about 32.2 mg/kg of body weight, i.p.

With respect to the activity of ketones of Formula (II), the compound produced in Example 5a showed an $ED_{50}$ of about 55 mg/kg p.o. in the Mouse Acetylcholine Writhing Assay.

Based on the above results, compounds of the invention may be used to treat mild to moderately severe pain in warm-blooded animals such as humans in a manner similar to the use of meperidine hydrochloride by administration of an analgesically effective dose. The dosage range would be from about 30 to 400 mg, in particular about 30 to 80 mg to about 300 to 400 mg, of active ingredient 1 to 4 times per day for an average (70 kg) human although it is apparent that activity of individual compounds of the invention will vary as will the pain being treated.

To prepare the pharmaceutical compositions of this invention, one or more compounds or salt thereof of the invention having Formula (I) or (II) as the active ingredient, is intimately admixed with a pharmaceutical carrier according to conventional pharmaceutical compounding techniques, which carrier may take a wide variety of forms depending on the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, from about 10 to about 500 mg of the active ingredient.

In the following Examples and throughout the specification, the following abbreviations may be used: mg (milligrams); g (grams); kg (kilograms); ml (milliliters); psi (pounds per square inch); mp (melting point); Et (ethyl); E (trans); Z (cis); $Et_2O$ (diethylether); EtOH (ethanol); p.o. (per os, orally); i.p. (intraperitoneal); hplc (high pressure liquid chromatography); hr (hours); N (normal); min (minutes); and C,H,N,O, etc. (the chemical symbols for the elements). Unless otherwise indicated, all temperatures are reported in °C. (degrees centigrade) and all references to ether are to $Et_2O$.

EXAMPLE 1 a. 5-Cyclohexylhexahydro-7(8H)-indolizinone
(Formula (II): A=cyclohexyl; n=0; x=0)

To a solution of 53.2 g (0.33 mole of 90% technical grade) of 4-aminobutyraldehyde diethyl acetal in 300 ml of absolute ethanol were added 112 ml of 3N hydrochloric acid, 33.6 g (0.3 mole) of cyclohexanecarboxaldehyde and 60.7 (0.3 mole) of diethyl 1,3-acetonedicarboxylate. The reaction solution was allowed to stir at room temperature for four days. Then, 23 g (0.175 mole) of solid potassium carbonate and 100 ml of distilled water were added and the reaction mixture partitioned between ether and water. The ether layer was extracted with 500 ml of 6N hydrochloric acid. This aqueous acid solution was heated to 95° C. while boiling off ether and ethanol, then the solution was refluxed with stirring overnight. The reaction solution was cooled to room temperature, made basic with 3N sodium hydroxide and extracted with ether. The ether layer was dried ($K_2CO_3$) and evaporated in vacuo to give 21.2 g of an oil. The oil was flash chromatographed on silica using 95% hexane, 5% acetone as the eluant. The first major compound bearing fraction was taken and the solvent evaporated in vacuo to give 4.1 g (6.2% yield) of the title compound as a water white oil.

b. 5-Cyclohexyloctahydroindolizine hydrochloride
(Formula (I): A=cyclohexyl; n=0; x=0)

To a solution of 3.29 (0.0135 mole) of trans-5-cyclohexyl-7(8H)-indolizinone, the compound of Example 1a, in 50 ml of 2-hydroxyethyl ether was added 0.92 ml (0.0135 mole) of anhydrous hydrazine and 1.6 g (0.0289 mole) of potassium hydroxide, and heated on the steam bath with stirring for 1 hr. The reaction mixture was then heated so that it distilled at 160°–175° C. over a 2.5 hr period. After about 30 ml had been collected, the heat was removed. The distillate was partitioned between ether and water. The ether layer was dried ($K_2CO_3$) and evaporated in vacuo in give 2.6 g of an oil. The oil was flash chromatographed on silica using 90% hexane, 10% acetone as the eluant. The first major compound bearing fractions were pooled and the solvent evaporated to give 2.1 g of an oil. The oil was dissolved in dry ether, treated with ethereal hydrogen chloride and recrystallized from acetonitrile to give 1.4 g (47% yield) of the title compound as a white solid, mp=248°–249° C.

EXAMPLE 2 a. Hexahydro-5-(2-phenylethyl)-7(8H)-indolizinone
(Formula (II): A=phenyl; n=2; x=0)

To a solution of 66 g (0.368 mole of 90% technical grade) of 4-aminobutyraldehyde diethyl acetal in 300 ml of absolute ethanol were added 138 ml of 3N hydrochloric acid, 75.3 g (0.372 mole) of diethyl-1,3-acetonedicarboxylate and 50 g (0.373 mole) of hydrocinnamaldehyde. The reaction solution was stirred at room temperature for seven days. Then the reaction mixture was partitioned between ether and water. The ether layer was extracted with 650 ml of 6N hydrochloric acid. This aqueous acid solution was heated to 95° C. while boiling off ether and ethanol, then the solution was refluxed with stirring overnight. The reaction solution was cooled to room temperature, made basic with 3N sodium hydroxide, and extracted with ether. The ether layer was dried ($K_2CO_3$), then evaporated in vacuo to a brown oil (12.6 g). The oil was flash chromatographed on silica using 85% hexane, 15% acetone as the eluant. The first major compound bearing fraction was taken and the solvent evaporated in vacuo to give 4 g (4.4% yield) of the title compound as an oil.

b. Octahydro-5-(2-phenylethyl)indolizine hydrochloride (Formula (I): A=phenyl; n=2; x=0)

To a solution of 4 g (0.0166 mole) of trans-hexahydro-5-phenylethyl)-7(8H)-indolizinone, the compound of Example 2a, in 40 ml of 2-hydroxyethyl ether were added to 1.05 g (0.033 mole) of anhydrous hydrazine and 2.8 g (0.0499 mole) of potassium hydroxide. The reaction mixture was refluxed with stirring in a flask fitted with a Dean-Starke trap wrapped with heating tape and the refluxing continued for 3.5 h. The mixture was cooled to room temperature, water added and the mixture extracted with ether. The ether layer was washed with brine, dried ($K_2CO_3$), and evaporated in vacuo to an oil. The oil was treated with ethereal hydrogen chloride, and the salt recrystallized from acetonitrile. After a second recrystallization from acetonitrile, 520 mg of the title compound was obtained as a grey solid (11.8% yield), mp 162°–164° C.

EXAMPLE 3 a. 5-(4-Bromophenyl)hexahydro-7(8H)-indolizinone
(Formula (II): A=phenyl; $R^1$=4-bromo; n=0; x=1)

To a solution of 96.8 g (0.54 mole of 90% technical grade) of 4-aminobutyraldehyde diethyl acetal in 400 ml of absolute ethanol were added 200 ml of 3N hydrochloric acid, 109.2 g (0.54 mole) of diethyl 1,3-acetonedicarboxylate and 100 g (0.54 mole) of 4-bromobenzaldehyde. The reaction mixture was cooled at room temperature, made basic with 3N sodium hydroxide and extracted with ether. The ether layer was dried ($K_2CO_3$) and the ether was evaporated in vacuo to give 61 g of an oil. The oil was flash chromatographed on silica using 95% hexane, 5% acetone as the eluant. The first major compound bearing fractions were pooled to give 14.7 g (9.3% yield) of the title compound as an oil.

b. 5-(4-Bromophenyl)octahydroindolizine hydrochloride (Formula (I): A=phenyl; R$^1$=4-bromo; n=0; x=1)

To a solution of 14.7 g (0.05 mole) of trans-5-(4-bromophenyl)hexahydro-7(8H)-indolizone, the compound of Example 3a, in 150 ml of 2-hydroxyethyl ether was added 3.2 ml (0.1 mole) of anhydrous hydrazine and the mixture heated on a steam bath for 1 hr. Then, 5.6 g (0.1 mole) of potassium hydroxide was added to the reaction mixture and heated to reflux with stirring. The flask was fitted with a Claisen distillation head and the mixture began to distill at 120° C. and continued over a 1.25 hr period until a final temperature of 235° C. had been reached and 75 ml had come over. This distillate was partitioned between water and ether. The ether layer was dried (K$_2$CO$_3$), and the ether evaporated in vacuo to give 9 g of a white oil. A lower boiling fraction was distilled off under reduced pressure. The oil from the pot residue (6.9 g) was treated with ethereal hydrogen chloride and the salt recrystallized from isopropanol to give 4.4 g (27.9% yield) of the title compound as a white solid, m.p. 264°–267° C.

EXAMPLE 4 a. 5-(2,4-Dichlorophenyl)hexahydro-7(8H)-indolizinone (Formula (II): A=phenyl; R$^1$=2,4-diCl$_2$; n=0 x=2)

To a solution of 50 g (0.28 mole of 90% technical grade) of 4-aminobutyraldehyde diethyl acetal in 300 ml of absolute ethanol was added 100 ml of 3N hydrochloric acid 50 g (0.29 mole) of 2,4-dichlorobenzaldehyde and 57.8 g (0.29 mole) of diethyl 1,3-acetonedicarboxylate.

The reaction mixture was stirred at room temperature for 11 days. The mixture was then partitioned between water and ether. The ether layer was extracted with 516 ml of 6N hydrochloric acid. The acid solution was heated to 95° C. with ether and ethanol boiling off, then refluxed with stirring overnight. The reaction mixture was cooled to room temperature, made basic with 10% sodium hydroxide and extracted with ether. The ether layer was dried (K$_2$CO$_3$) and the ether evaporated in vacuo to give 34 g of an oil. The oil was flash chromatographed on silica using 85% hexane, 15% ethyl acetate as the eluant. The first major compound bearing fraction was taken and the solvent evaporated in vacuo to give 4.9 g of the title compound as an oil (6.4% yield).

b. 5-(2,4-Dichlorophenyl)octahydroindolizine hydrochloride (Formula (I): A=phenyl; R$^1$=2,4diCl$_2$; n=O; x=2)

To a solution of 4.9 g (0.018 mole) of trans-5-(2,4-dichlorophenyl)hexahydro-7(8H)-indolizinone, the compound of Example 4a, in 50 ml of 2-hydroxyethyl ether was added 1.14 ml (0.036 mole) of anhydrous hydrazine and 3 g (0.054 mole) of potassium hydroxide. The mixture was heated to reflux in a flask fitted with a heated Dean Starke trap for 4 hr. The reaction mixture was cooled to room temperature and partitioned between water and ether. The ether layer was dried (K$_2$CO$_3$) and the ether evaporated in vacuo to an oil. The oil was flash chromatographed on silica using 95% hexane, 5% ethyl acetate as the eluant. The first major compound bearing fractions were combined and the solvent evaporated in vacuo to give 600 mg of an oil. The oil was treated with ethereal hydrogen chloride, and the salt recrystallized from acetonitrile to give 270 mg of the title compound as a grey solid (4.9% yield), mp=272°–277° C.

EXAMPLE 5 a. 5-(2-Bromophenyl)hexahydro-7(8H)-indolizinone (Formula (II): A=phenyl; R$^1$=2−Br; n=0; x=1)

To a solution of 57.3 g (0.32 mole) of 4-aminobutyraldehyde diethyl acetal in 200 ml of absolute ethanol was added 107 ml of 3N hydrochloric acid, and 65.6 g (0.32 mole) of diethyl 1,3-acetonedicarboxylate and 60 g (0.32 mole) of 2-bromobenzaldehyde were quickly added. The reaction mixture was stirred at room temperature for five days. Then the mixture was partitioned between water and ether. The ether layer was extracted with 530 ml of 6N hydrochloric acid. The acid solution was heated to 95° C. with ether and ethanol boiling off, then reflux with stirring overnight. The reaction was cooled to room temperature, made basic with 3N sodium hydroxide and extracted with ether. The ether layer was dried (MgSO$_4$) and the ether was evaporated in vacuo to give 35 g of a brown oil. The oil was flash chromatographed on silica using 85% hexane, 15% ethyl acetate as the eluant. The first major compound bearing fractions were combined and the solvent evaporated in vacuo to an oil. The oil was treated with ethereal hydrogen chloride, and the salt recrystallized from acetonitrile to give 5.9 g of a white solid (5.5% yield), mp=171°–172.5° C.

b. 5-(2-Bromophenyl)-1,2,4,5,6-(1,2,4,5,8)Hexahydroindolizine hydrochloride (Formula (IV))

Amalgamated zinc was prepared by dissolving 3.13 g (0.012 mole) of mercuric chloride in a solution of 3.1 ml of concentrated hydrochloric acid in 93.8 ml of water, then zinc dust 7.5 g (0.11 mole) was added and the mixture shaken for five minutes. The supernatant solution was decanted off, and the zinc amalgam added to a mixture of 5 g (0.015 mole) of trans-5-(2-bromophenyl)-hexahydro-7(8H)-indolizinone hydrochloride, the compound of Example 5a, in 100 ml of 6N hydrochloric acid. The mixture was refluxed with stirring for 3 hr. Then the reaction mixture was cooled to room temperature, made basic with 10% sodium hydroxide and extracted with ether. The ether layer was dried (K$_2$CO$_3$) and the ether evaporated in vacuo to an oil (2.5 g). The oil was flash chromatographed on silica using 95% hexane, 5% ethyl acetate as the eluant. The first major compound bearing fractions were combined and the solvent evaporated to give 1.6 g of an oil. The oil was treated with ethereal hydrogen chloride and the salt recrystallized from acetonitrile to give 800 mg (16% yield) of the title compound, mp=221° C.

c. 5-(2-Bromophenyl)octahydroindolizine hydrochloride (Formula (I): A=phenyl; R$^1$=−Br; n=0; x=1)

A 680 mg (0.002 mole) sample of trans-5-(2-bromophenyl)-1,2,4,5,6-(1,2,4,5,8)-hexahydroindolizine hydrochloride, the compound of Example 5b, was dissolved in 20 ml of glacial acetic acid and 20 mg of platinum oxide added. The mixture was placed on the Paar apparatus under 49 psi of hydrogen and shaken for one hour. The drop in hydrogen pressure was 1.9 psi. The platinum oxide was filtered off and the acetic acid solution was made basic with 3N sodium hydroxide and extracted with ether. The ether layer was dried ($K_2CO_3$), and the ether evaporated in vacuo to a yellow oil. The oil was flash chromatographed on silica using 90% hexane, 10% ethyl acetate as the eluant. The first major compound bearing fractions were combined, and the solvent evaporated in vacuo to give a white oil. The oil was treated with ethereal hydrogen chloride, and the salt recrystallized from acetonitrile to give 175 mg of the title compound a white solid mp=223°–5° C.

EXAMPLE 6 & 7

Following the procedure of Example 4a and employing equivalent quantities of diethyl 1,3-acetonedicarboxylate, 4-aminobutyraldehyde diethyl acetal, and appropriate aldehyde of formula (II), the following trans-5-arylhexahydro-7(8H)-indolizinone compounds of formula (III) analogous to the product of Example 4a were obtained represented below as 6a and 7a. Subsequent reduction of these products using Wolff-Kishner conditions according to the procedure of Example 4b afforded 5-aryloctahydroindolizines of the trans-5, 8a stereochemical family of the formula (I) designated below as the products of Example 6b and 7b.

| Example | | mp °C. | Form |
| --- | --- | --- | --- |
| 6a | 2,4-di-$CH_3$—phenyl | — | base (oil) |
| 6b | 2,4 di-$CH_3$—phenyl | 262–264° C. | HCl |
| 7a | 3-$CF_3$—phenyl | — | base (oil) |
| 7b | 3-$CF_3$—phenyl | 202–204° C. | HCl |

EXAMPLE 8

N-[[[4-(trans-Octahydro-5-indolizinyl)phenyl]thio]-phenyl]acetamide hydrochloride hydrate (50:50:33) (Formula (I): A=phenyl: $R^1$=4-acetaminophenylthio: n=0: x=1)

A 1.01g (0.021 mole) sample of a 50% suspension of sodium hydride in oil was washed with hexane and the hexane washings discarded. Then 25 ml of argon degassed n-butanol was added dropwise and stirring continued until all the sodium hydride had been consumed. A warmed, filtered solution of 3.9g (0.023 mole of 90% technical grade) p-acetamidothiophenol in 75 ml of n-butanol was added in portions to the sodium butoxide solution portionwise with stirring at room temperature. A 5.9 g (0.021 mole) sample of trans-5(4-bromophenyl) octahydroindolizine, the compound of Example 3b converted to its free base, and a 970 mg (0.008 mole) sample of tetrakis (triphenylphosphine) palladium (0) were added to the reaction mixture and the mixture was refluxed with stirring under nitrogen overnight. In a separate flask a 1g (0.02 mole) sample of a 50% suspension of sodium hydride in oil was washed with hexane and the hexane washings discarded. Then 20 ml of argon degassed n-butanol was added dropwise. To the subsequent solution, a warmed solution of 3.9 g (0.023 mole) of p-acetamidothiophenol in 100 ml of n-butanol was added portionwise with stirring at room temperature. A sample of 980 mg (0.008 mole) of tetrakis (triphenylphosphine) palladium (0) was then added to the original reaction mixture containing the 5.9 g sample of trans-5-(4-bromophenyl) octahydroindolizine and the mixture was heated to reflux. Then the solution of freshly prepared sodium salt of p-acetamidothiophenol was added dropwise over 1.5 hr. The reaction mixture was refluxed with stirring for an additional 3 h after the addition was completed. The reaction was cooled to room temperature and the reaction mixture was filtered. The n-butanol of the filtrate was evaporated in vacuo, and the semisolid residue partitioned between water and ether. The ether layer was extracted with 3N hydrochloric acid, the acid layer was washed with ether, the ether washings discarded, and the acid layer was made basic with 3N sodium hydroxide. After extracting the basic layer with ether, the ether layer was dried ($K_2CO_3$) and evaporated in vacuo to 3.6 g of a tan oil. The oil was flash chromatographed on silica using 75% hexane, 25% acetone as the eluant. The first major compound bearing fractions were combined and the solvent evaporated in vacuo to give 2.9 g of an oil. The oil was chromatographed on a Waters Prep 500 preparative hplc unit using 85% hexane, 15% acetone as the eluant. The first major compound bearing fractions were pooled to give 2.3 g (30% yield) of an oil. The oil was treated with ethereal hydrogen chloride and the salt dried without recrystallization to give 1.89 g of the title compound, a white solid, mp=88°–140° C. dec.

What is claimed:

1. An octahydroindolizine of the following formula (I)

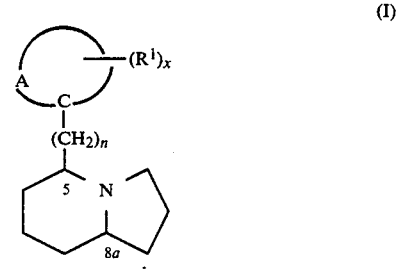

wherein

A represents the atoms necessary to form a phenyl, naphthyl, cycloalkyl or cycloalkenyl ring system as the A-C cycle shown in formula (I):

$R^1$ is independently alkyloxy, alkylthio: phenylthio; or phenylthio substituted by acetamido, halo or alkyl:

n is the integer 0, 1, 2, 3, 4, 5, or 6: and x is the integer 0, 1, 2, or 3, provided that when A is phenyl and n is 0, x is 1, 2 or 3, and the pharmaceutically-acceptable acid-addition salts thereof.

2. The octahydroindolizine of claim 1, wherein said cycloalkyl for A is cycloalkyl of about 3 to 7 carbons: said cycloalkenyl for A is cycloalkenyl of about 3 to 7 carbons: said halogen for substitution on phenylthio for $R^1$ is fluoro, chloro, bromo or iodo: and the alkyl portion of said alkyloxy and alkylthio is of about 1 to 8 carbons.

3. The octahydroindolizine of claim 1, wherein the 5-position substituent and the 8a position hydrogen of formula (I) are trans to each other.

4. The octahydroindolizine of claim 3, wherein the hydrogen atom at the 5 positions of formula (I) is an alpha hydrogen.

5. The octahydroindolizine, of claim 3, wherein the hydrogen atom at the 5 position of formula (I) is a beta hydrogen.

6. The octahydroindolizine of claim 1, wherein the 5-position substituent and the 8a position hydrogen of formula (I) are cis to each other.

7. The octahydroindolizine of claim 1, wherein A represents the atoms necessary to form a phenyl ring and n is 0, 1 or 2.

8. The octahydroindolizine of claim 7, wherein n is 0, x is 1, 2 or 3 and at least one $R^1$ group is at the ortho position of the phenyl ring.

9. The octahydroindolizine of claim 8, wherein x is 1 and the $R^1$ group is at the ortho position of the phenyl ring.

10. The octahydroindolizidine of claim 1, wherein said octahydroindolizidine is selected from the group consisting of:
5-cyclohexyloctahydroindolizine,
octahydro-5-(2-phenylethyl)indolizine, and
N[[[4-(trans-octahydro-5-indolizinyl)phenyl]thio]phenyl] acetamide.
or a pharmaceutically-acceptable acid-addition salt thereof.

11. The octahydroindolizine of claim 10, wherein said octahydroindolizine is trans.

12. The octahydroindolizine of claim 1, which is N-[[[4-(trans-octahydro-5-indolizinyl) phenyl]thio]-phenyl]acetamide or a pharmaceutically-acceptable acid-addition salt thereof.

13. A pharmaceutical composition effective in the treatment of pain which comprises a pharmaceutically-acceptable carrier and a pain-reducing amount of an octahydroindolizine of the following formula (I):

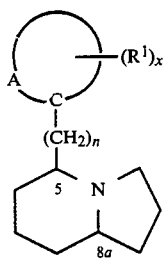

(I)

wherein
A represents the atoms necessary to form a ring system selected from the group consisting of phenyl, naphthyl, cycloalkyl or cycloalkenyl, as the A-C cycle shown in formula (I);
$R^1$ is independently alkyloxy, alkylthio; phenylthio; or phenylthio substituted by acetamido, halo or alkyl;
n is the integer 0, 1, 2, 3, 4, 5 or 6; and
x is the integer 0, 1, 2 or 3,
and the pharmaceutically-acceptable acid-addition salts thereof.

14. The pharmaceutical composition of claim 13, wherein said cycloalkyl for A is cycloalkyl of about 3 to 7 carbons; said cycloalkenyl for A is cycloalkenyl of about 3 to 7 carbons; said halogen for substitution in phenylthio for $R^1$ is fluoro, chloro, bromo or iodo; and the alkyl portion of said alkyloxy and alkylthio is of about 1 to 8 carbons.

15. The pharmaceutical composition of claim 13, wherein said octahydroindolizine is selected from the group consisting of:
5-cyclohexyloctahydroindolizine,
octahydro-5-(2-phenylethy)indolizine,
N[[[4-(trans-octahydro-5-indolizinyl)phenyl]thio]-phenyl]acetamide.

or a pharmaceutically-acceptable acid-addition salt thereof.

16. The pharmaceutical composition of claim 13, wherein said octahydroindolizine is the trans-octahydroindolizine.

17. A method of relieving pain in a mammal which comprises administering to the mammal a pharmaceutical composition effective in the treatment of pain which comprises a pharmaceutically-acceptable carrier and a pain-reducing amount of an octahydroindolizine of the following formula (I):

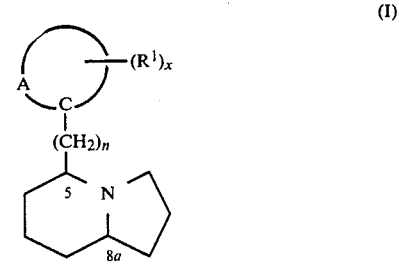

wherein
A represents the atoms necessary to form a ring system selected from the group consisting of phenyl, naphthyl, cycloalkyl or cycloalkenyl as the A-C cycle shown in formula (I);
$R^1$ is independently phenylthio; or phenylthio substituted by acetamido, halo or alkyl;
n is the inter 0, 1, 2, 3, 4, 5 or 6; and
x is the integer 0, 1, 2 or 3,
and the pharmaceutically-acceptable acid-addition salts thereof.

18. The method of claim 17, wherein said mammal is a human.

19. A ketone of the following formula (II)

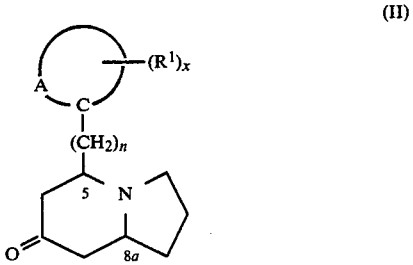

(II)

wherein
A represents the atoms necessary to form a phenyl, naphthyl, cycloalkyl or cycloalkenyl ring system as the A-C cycle shown in formula (I):
$R^1$ is independently cyano, halogen, alkyl, alkyloxy, alkylthio; phenylthio; phenylthio substituted by acetamido, halo or alkyl; haloalkyl; alkenyl; alkynyl; cycloalkenyl; or alkyl, alkenyl or alkynyl substituted by hydroxy;
n is the integer 0, 1, 2, 3, 4, 5 or 6; and
x is the integer 0, 1, 2 or 3, provided that when A is phenyl and n is 0, x is 1, 2 or 3,
and the pharmaceutically-acceptable acid-addition salts thereof.

20. The ketone of claim 19, wherein said clcloalkyl for A is cycloalkyl of about 3 to 7 carbons; said cycloalkenyl for A is cycloalkenyl of about 3 to 7 carbons; said halogen for $R^1$ and for substitution on phenylthio for $R^1$ is fluoro, chloro, bromo or iodo; the alkyl portion of said alkyl, alkyloxy, alkylthio, haloalkyl and substituted alkyl for $R^1$ is of about 1 to 8 carbons; the alkenyl portion of said alkenyl and substituted alkenyl for $R^1$ is of about 2 to 8 carbons; the alkynyl portion of said alkynyl and substituted alkynyl for $R^1$ is of about 2 to 8 carbons; the halo portion of said haloalkyl for $R^1$ is one or more of fluoro, chloro, bromo or iodo atoms; and said cycloalkenyl for $R^1$ is cycloalkenyl of 3 to 7 carbons.

21. The ketone of claim 19, wherein said ketone is selected from the group consisting of:
5-cyclohexylhexahydro-7(8H)-indolizinone,
hexahydro-5-(2-phenylethyl)-7(8H)-indolizinone,
5-(4-bromophenyl)hexahydro-7(8H)-indolizinone,
5-(2,4-dichlorophenyl)hexahydro-7(8H)-indolizinone,
5-(2-bromophenyl)hexahydro-7(8H)-indolizinone,
5-(2,4-dimethylphenyl)hexahydro-7(8H)-indolizinone, and
hexahydro-5-[7(8H)]-indolizinone.

22. The ketone of claim 19, wherein said ketone is the trans-ketone.

23. A pharmaceutical composition effective in the treatment of pain which comprises a pharmaceutically-acceptable carrier and a pain reducing amount of a ketone of the following formula (II):

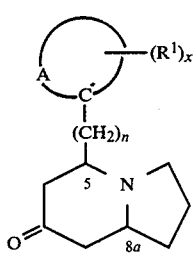

(II)

wherein
A represents the atoms necessary to form a ring system selected from the group consisting of phenyl, naphthyl, cycloalkyl or cycloalkenyl as the A-C cycle shown in formula (II);
$R_1$ is independently cyano, halogen, alkyl, alkyloxy, alkylthio; phenylthio; phenylthio substituted by acetamido, halo or alkyl; haloalkyl; alkenyl; alkynyl; cycloalkenyl; or alkyl, alkenyl or alkynyl substituted by hydroxy;
n is the integer 0, 1, 2, 3, 4, 5 or 6; and
x is the integer 0, 1, 2 or 3,
and the pharmaceutically-acceptable acid-addition salts thereof.

24. The pharmaceutical composition of claim 23, wherein said cycloalkyl for A is cycloalkyl of about 3 to 7 carbons; said cycloalkenyl for A is cycloalkenyl of about 3 to 7 carbons; said halogen for $R^1$ and for substitution in phenylthio for $R^1$ is fluoro, chloro, bromo or iodo; the alkyl portion of said alkyl, alkyloxy, alkylthio, haloalkyl and substituted alkyl for $R^1$ is of about 1 to 8 carbons; the alkenyl portion of said alkenyl and substituted alkenyl for $R^1$ is of about 2 to 8 carbons; the alkynyl portion of said alkynyl and substituted alkynyl for $R^1$ is of about 2 to 8 carbons; the halo portion of said haloalky for $R^1$ is one or more of fluoro, chloro, bromo or iodo atoms; and said cycloalkenyl for $R^1$ is cycloalkenyl of 3 to 7 carbons.

25. The pharmaceutical composition of claim 23, wherein said ketone is selected from the group consisting of:
5-cyclohexylhexyahydro-7(8H)-indolizinone,
hexahydro-5-(2-phenylethyl)-7(8H)-indolizinone,
5-(4-bromophenyl)hexahydro-7(8H)-indolizinone,
5-(2,4-dichlorophenyl)hexahydro-7(8H)-indolizinone,
5-(2-bromophenyl)hexahydro-7(8H)-indolizinone,
5-[(2,4-dimethylphenyl)hexahydro]-7(8H)-indolizinone, and
hexahydro-5-7(8H)-indolizinone.

26. The pharmaceutical composition of claim 23, wherein said ketone is the trans-ketone.

27. A method of relieving pain in a mammal which comprises administering to the mammal the pharmaceutical composition of claim 23.

* * * * *